(12) United States Patent
Biedermann et al.

(10) Patent No.: US 6,972,043 B1
(45) Date of Patent: Dec. 6, 2005

(54) FOOT PROSTHESIS

(75) Inventors: Lutz Biedermann, Villingen (DE); Urs Schneider, Tübingen (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 09/914,256

(22) PCT Filed: Nov. 24, 2000

(86) PCT No.: PCT/EP00/11717

§ 371 (c)(1),
(2), (4) Date: Aug. 22, 2001

(87) PCT Pub. No.: WO01/47444

PCT Pub. Date: Jul. 5, 2001

(30) Foreign Application Priority Data

Dec. 24, 1999 (DE) ................................. 199 62 851

(51) Int. Cl.[7] ................................................ A61F 2/66
(52) U.S. Cl. ....................................................... 623/55
(58) Field of Search ............................. 623/55, 54, 53, 623/47, 49, 56

(56) References Cited

U.S. PATENT DOCUMENTS

| | | | |
|---|---|---|---|
| 4,547,913 A | 10/1985 | Phillips | 623/27 |
| 4,822,363 A | 4/1989 | Phillips | 623/27 |
| 5,116,384 A | 5/1992 | Wilson et al. | 623/49 |
| 5,258,039 A | 11/1993 | Goh et al. | 623/55 |
| 5,376,139 A * | 12/1994 | Pitkin | 623/51 |
| 5,443,528 A | 8/1995 | Allen | 623/52 |
| 5,653,767 A | 8/1997 | Allen et al. | 623/52 |
| 5,800,570 A | 9/1998 | Collier | 623/55 |
| 5,944,760 A * | 8/1999 | Christensen | 623/55 |
| 6,602,295 B1 * | 8/2003 | Doddroe et al. | 623/55 |

FOREIGN PATENT DOCUMENTS

| | | |
|---|---|---|
| DE | 297 07 416 U1 | 8/1998 |
| DE | 298 20 904 U1 | 4/1999 |
| DE | 298 23 435 U1 | 7/1999 |
| DE | 299 20 434 U1 | 4/2000 |

* cited by examiner

*Primary Examiner*—Alvin J. Stewart
(74) *Attorney, Agent, or Firm*—Barley Snyder LLC

(57) ABSTRACT

There is provided a foot prosthesis having especially good gait characteristics. To that end, the prosthesis comprises a first spring element 1 extending from the toe region to the lower leg region and a second spring element 2 extending from the heel region to the lower leg region. The spring elements are formed as leaf-type elements and are connected to each other by their lower leg side first ends 4, 7. There is provided a tension element 9 which is connected in the forward region of the foot with its one end and connected in the heel region 6 to the second spring element.

15 Claims, 2 Drawing Sheets

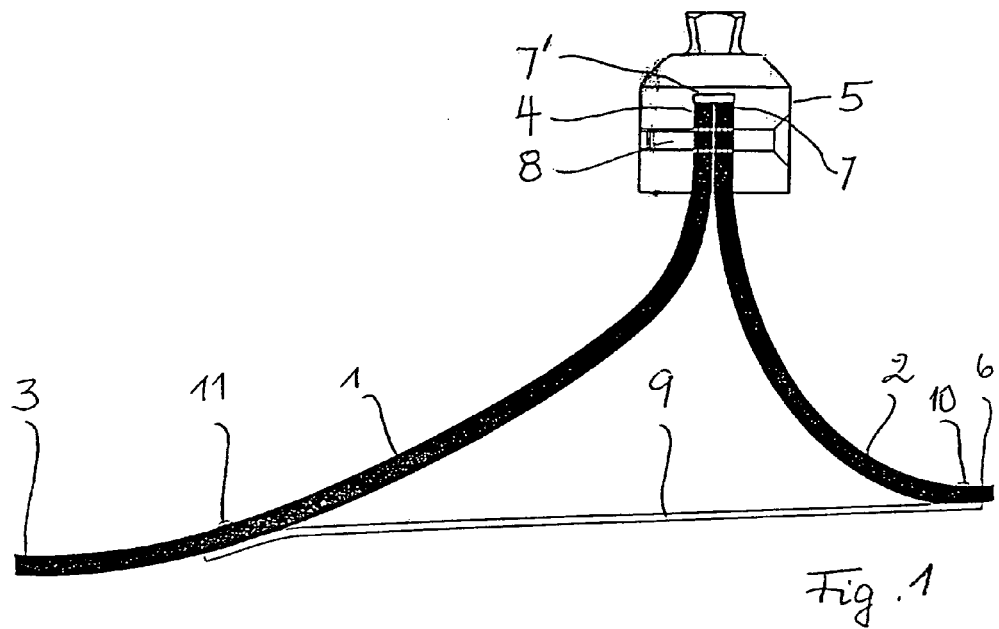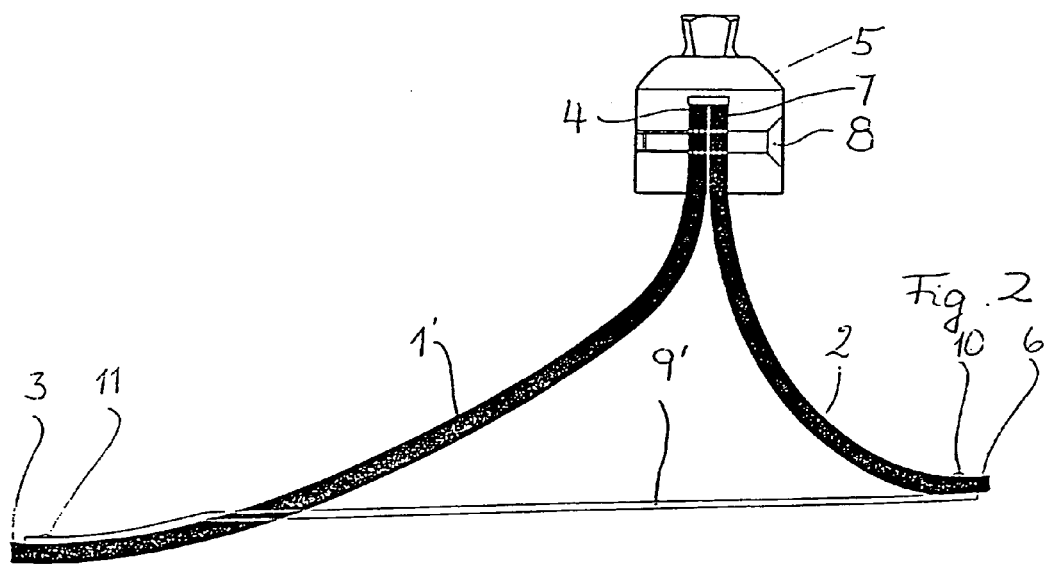

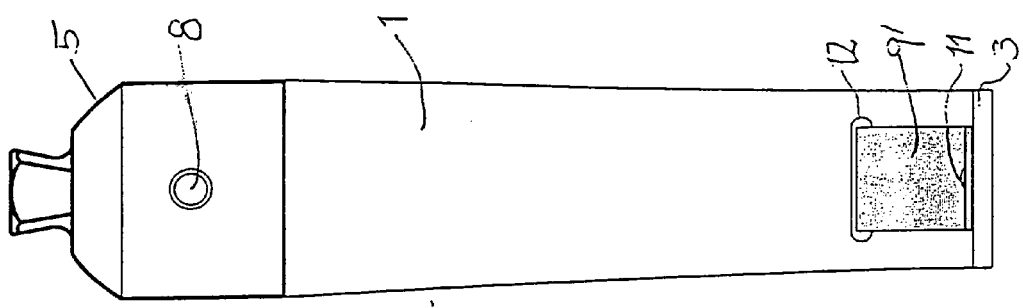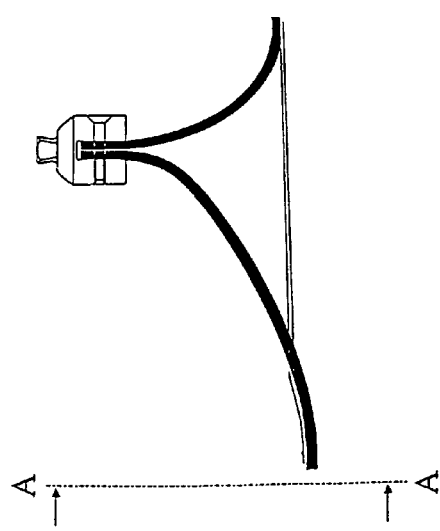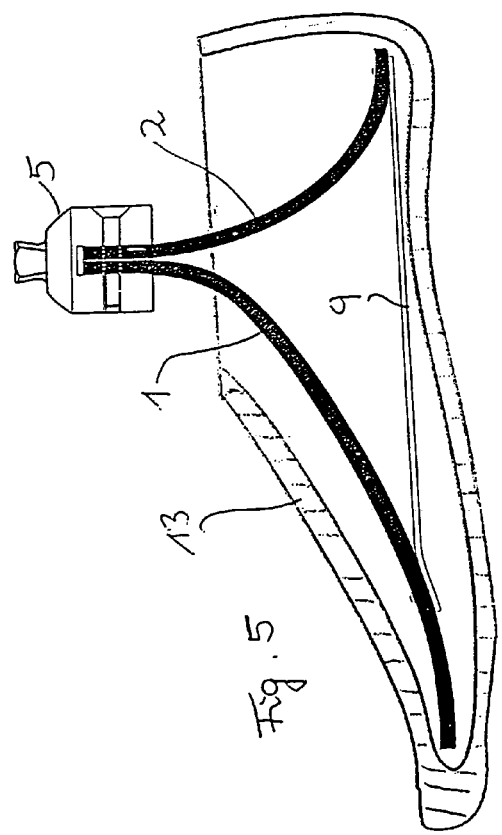

FOOT PROSTHESIS

The invention relates to a foot prosthesis. From the brochure BIEDERMANN MOTECH, Unterschenkel-Systeme (lower leg systems), page 15, a foot prosthesis is known which is formed by a first spring element and a second spring element connected thereto. The first spring element extends from the toe region to the lower leg region and is formed in a convex fashion as viewed from the top. In the lower leg region the free end supports an adapter for connecting to the lower leg element of a prosthesis. In the region around the ball of the foot the spring element is firmly connected on its lower side to the upper side of the front foot side end of a second spring element by means of screws, which second spring element extends with its free end to the toe region. The first spring element consists of a carbon fiber composite material and has the appearance of a leaf spring having a width of about 4 cm in the ball region and a thickness of 3 to 4 mm.

It is an object of the invention to provide a foot prosthesis with even better gait characteristics.

This object is achieved by a foot prosthesis according to claim 1.

Further embodiments of the invention are characterized in the dependent claims.

Further features and advantages of the invention will be apparent from the description of embodiments with respect to the figures, where FIG. 1 is a lateral view of a first embodiment of the invention;

FIG. 2 is a corresponding lateral view of a second embodiment;

FIG. 3 is an illustration similar to the one in FIG. 2;

FIG. 4 is a plan view of the object shown in FIG. 3 in the direction of arrows A'-A; and FIG. 5 shows the object shown in FIG. 1 in an artificial foot represented in section.

The first embodiment shown in FIG. 1 comprises a first spring element 1 and a second spring element 2. Each of the spring elements is formed in a concave fashion as viewed from the top. The first spring element 1 extends with one free end 3 from the toe region to its opposite free end 4 which is held in an adapter 5 that can be connected to the lower leg portion of a prosthesis. The second spring element 2 extends with one of its free ends 6 from the heel to its other free end 7 which is held in the adapter 5.

The bending of the two spring elements is selected such that in their inoperative position the two ground-side free ends 3, 6 are supported flat on the ground and the opposite free ends 4, 7 abut in parallel fashion with their convex-side surface, as can be seen in the figure, and are held in a slot 7' of the adapter 5 and are fixed in the adapter 5 by a locking screw 8.

As can be seen from the figures, the front foot region of the first spring element 1 and the heel region of the second spring element 2 are connected to each other through a tension element 9. As can be best seen in FIG. 4, the tension element is formed in a ribbon-like manner and is formed as a stretch-free tension ribbon. The tension element 9 is connected in a tension-proof fashion with one of its ends as close as possible to the free end 6 of the second spring element 2 using rivets 10 and with its other free end close to the free end of the first spring element 1 using rivets 11. The connection location of the rivets 11 is selected such that the first spring element 1 in its normal position is still located a distance from the ground. This provides the advantage that during the walking the tension element 9 does not always rest on the ground and will thus be spared. The connecting location with the rivets 11 should be as close as possible to the free end 3 of the first spring element.

The foot prosthesis formed in this manner provides for especially advantageous gait characteristics starting by setting the foot in its heel region on the ground and finishing with a rolling movement through the front foot.

The embodiment shown in FIG. 2 coincides with respect to the shape of the spring elements, the connection to the adapter and the provision of a tension element.

In order to achieve the advantage that the tension element 9' is fixed as close as possible to the free ends 3, 6 using the rivets 10, 11 and that the tension element acts on the outermost free ends on the one hand, and the advantage that the tension element does not completely rest on the ground on the other hand, there is provided, a distance from the free end 3 where the first spring element 1 has just enough cleareance from the ground, a slit 12 extending along a direction transverse to the longitudinal direction of the first spring element 1', as can be best seen in FIG. 4. This slit is desigend to lead the tension element 9' across the slit 12 all the way to the forward free end 3 of the first spring element 1'. Starting from the slit 12, the tension element 9' is arranged in closely fitting relationship with the convex portion of the spring element 1' and is firmly connected thereto in the toe region by rivets 11, as is best seen in FIG. 2.

Alternatively, it is also possible to arrange the tension element 9 at the bottom surface of the first spring element 1 and all the way to the free end, if it is accepted that the tension element will then rest on the ground.

Referring to FIG. 5, the embodiment described first is introduced into an artificial foot 13 in a basically known fashion.

What is claimed is:

1. A foot prosthesis comprising:
    a first spring element having two free ends, the first free end extends from a toe region and the second free end extends to a lower leg region;
    a second spring element extending from a heel region to said lower leg region;
    said spring elements being connected to each other at said lower leg region; and
    a ribbon-like tension element having two ends, which is connected with its one end to a forward region of the first spring element and connected with its other end at said heel region of the second spring element,
    wherein said tension element is structured and arranged to be able to transmit only a tension force between its one end and its other end.

2. The foot prosthesis as claimed in claim 1, further comprising an adapter that connects the spring elements at the lower leg region for connection to a lower leg portion.

3. The foot prosthesis as claimed in claim 1, wherein said tension element is firmly connected to a ground-side of each of said spring elements.

4. The foot prosthesis as claimed in claim 1, wherein said first and second spring elements are formed as a concave shape when viewed from the top.

5. The foot prosthesis as claimed in claim 1, wherein said first and second spring elements comprise a carbon fiber composite material and said tension element comprises a stretch-free material.

6. The foot prosthesis as claimed in claim 1, wherein the first and second spring elements are each a leaf spring having a ground-side surface, the springs being arranged and structured to rest against each other with their ground-side surfaces facing each other.

7. The foot prosthesis as claimed in claim 6, wherein said tension element is firmly connected to the ground-side surface of the forward region of the first spring element and of the heel region of the second spring element.

8. The foot prosthesis as claimed in claim 6, wherein said tension element is fixed at the forward end of said first spring element on an upper side thereof such, said first spring element having a slit-like opening in said forward region through which said tension element is fed toward said second spring element.

9. The foot prosthesis as claimed in claim 1, wherein said tension element is fixed at the forward end of said first spring element on an upper side thereof such, said first spring element having a slit-like opening in said forward region through which said tension element is fed toward said second spring element.

10. A foot prosthesis comprising:
  a first spring element having two free ends, the first free end extends from a toe region and the second free end extends to a lower leg region;
  a second spring element extending from a heel region to said lower leg region;
  said spring elements being connected to each other at said lower leg region; and
  a ribbon-like tension element having two ends, which is connected with its one end to a forward region of the first spring element and connected with its other end at said heel region of the second spring element,
  wherein the first and second spring elements are each a leaf spring having a ground-side surface, the springs being arranged and structured to contact and rest against each other with their ground-side surfaces facing each other.

11. The foot prosthesis as claimed in claim 10, wherein said tension element is firmly connected to the ground-side surface of the forward region of the first spring element and of the heel region of the second spring element.

12. The foot prosthesis as claimed in claim 10, wherein said tension element is fixed at the forward end of said first spring element on an upper side thereof such, said first spring element having a slit-like opening in said forward region through which said tension element is fed toward said second spring element.

13. A foot prosthesis comprising:
  a first spring element extending from a toe region to a lower leg region;
  a second spring element extending from a heel region to said lower leg region;
  said spring elements being connected to each other at said lower leg region; and
  a tension element having two ends, which is connected with its one end to a forward region of the first spring element and connected with its other end at said heel region of the second spring element,
  wherein said tension element is fixed at the forward end of said first spring element on an upper side thereof such, said first spring element having a slit-like opening in said forward region through which said tension element is fed toward said second spring element.

14. The foot prosthesis as claimed in claim 13, wherein said first and second spring elements are formed as a concave shape when viewed from the top.

15. The foot prosthesis as claimed in claim 13, wherein said first and second spring elements comprise a carbon fiber composite material and said tension element comprises a stretch-free material.

* * * * *